(12) United States Patent
Young et al.

(10) Patent No.: US 6,316,492 B1
(45) Date of Patent: Nov. 13, 2001

(54) METHODS FOR TREATING OR PREVENTING VIRAL INFECTIONS AND ASSOCIATED DISEASES

(75) Inventors: Dorothy C. Young, Collegeville; Thomas R. Bailey, Phoenixville, both of PA (US)

(73) Assignee: Viropharma Incorporated, Exton, PA (US)

( * ) Notice: Subject to any disclaimer, the term of this patent is extended or adjusted under 35 U.S.C. 154(b) by 0 days.

(21) Appl. No.: 09/405,631

(22) Filed: Sep. 24, 1999

Related U.S. Application Data

(60) Provisional application No. 60/101,813, filed on Sep. 28, 1998.

(51) Int. Cl.[7] .......................... A61K 31/38; A61K 31/70; A61K 38/21

(52) U.S. Cl. .......................... 514/443; 514/444; 514/445; 424/85.4

(58) Field of Search .................................. 514/443, 444, 514/445, 42; 474/854

(56) References Cited

U.S. PATENT DOCUMENTS 3,721,668 * 3/1973 Rufer et al. .......................... 260/240
4,288,437 * 9/1981 Engel et al. .......................... 424/246
5,061,605 * 10/1991 Kawamura et al. .................. 430/281

* cited by examiner

*Primary Examiner*—Russell Travers

(57) ABSTRACT

Methods are provided for the treatment and prophylaxis of viral infection and disease associated with such infection.

14 Claims, No Drawings

METHODS FOR TREATING OR PREVENTING VIRAL INFECTIONS AND ASSOCIATED DISEASES

This is application claims the benefit of U.S. Provisional Application No. 60/101,813 filed Sep. 28, 1998.

FIELD OF THE INVENTION

The present invention relates to methods for preventing and treating viral infections and the diseases associated therewith, particularly those viral infections and associated diseases caused by viruses within the Flaviviridae family.

BACKGROUND OF THE INVENTION

The Flaviviridae family consists of three genera and several viruses that are currently unassigned to specific genera. The hepacivirus genus includes the hepatitis C virus (HCV). Viruses such as GB virus-A and GB virus-A-like agents, GB virus-D and GBV-C or hepatitis G virus, while at present not formally classified within the hepacivirus genus, are closely related to HCV and represent unassigned members of the Flaviviridae family. Also within the Flaviviridae is the pestivirus genus, which includes bovine viral diarrhea viruses (BVDV), border disease viruses and classical swine fever virus, and the flavivirus genus, with viruses such as dengue, yellow fever, Japanese encephalitis and tick-borne encephalitis viruses.

Viruses within this family cause significant disease in human and animal populations. HCV is a major cause of human hepatitis globally. The World Health Organization estimates that 170 million people worldwide are presently infected with the virus. Most infections become persistent and about 60% of cases develop chronic liver disease. Chronic HCV infection can lead to development of cirrhosis, hepatocellular carcinoma and liver failure.

Interferon and interferon in combination with ribavirin are used in the U.S. for hepatitis due to HCV. These treatments are associated with improved serum enzyme response in some patients. The remainder are non-responsive to treatment. For responders, a sustained clinical improvement is seen in only a small percentage of patients; the majority of patients relapse upon cessation of treatment. Thus, the effectiveness of therapy for chronic hepatitis C is variable and its cure rate remains low. Moreover, therapy is often associated with considerable adverse effects.

Pestivirus infections of domesticated livestock cause significant economic losses worldwide. Pestiviruses cause a range of clinical manifestations including abortion, teratogenesis, respiratory problems, chronic wasting disease, immune system dysfunction and predisposition to secondary viral and bacterial infections. Certain BVDV strains cause an acute fatal disease. BVDV can also establish persistent infected (PI) animals remain viremic throughout life and serve as continuous virus reservoirs. PI animals often succumb to fatal mucosal disease.

Flaviviruses are important pathogens of man and are also prevalent throughout the world. There are at least 38 flaviviruses associated with human disease, including the dengue fever viruses, yellow fever virus and Japanese encephalititis virus. Flaviviruses cause a range of acute febrile illnesses and encephalitic and hemorrhagic diseases.

Currently, there are no antiviral pharmaceuticals to prevent or treat pestivirus or flavivirus infections.

New therapies and preventatives are clearly needed for infections and diseases caused by viruses of Flaviviridae family.

In considering approaches to the diagnosis, control, prevention and treatment of infections and associated diseases caused by viruses, it is often desirable to identify virus-specific functions that may be exploited in such approaches. In particular, enzymatic activities of virus-encoded polypeptides are quite useful. These virus-specified components are often essential for virus replication and may be suitable targets for antiviral drug discovery strategies.

One such target that plays a central role in the life cycle of many RNA viruses is the virus-encoded RNA-dependent RNA polymerase (RdRp) protein. Regarding viruses of the Flaviviridae, this protein is termed NS5B in the case of the hepaciviruses and pestiviruses, and NS5 in the case of the flaviviruses (collectively referred to as NS5). RdRp proteins are a key component of the virus replicase complex, enabling the virus to replicate its RNA genome and produce progeny viruses. The RdRp of RNA viruses is an attractive target for antiviral drug development.

SUMMARY OF THE INVENTION

In accordance with the present invention, there is provided a method for treating viral infection and diseases asscoiated with such infection in a living host having such infection, by administering to such host a therapeutically effective amount of a compound, or a precursor thereof, having the following formula:

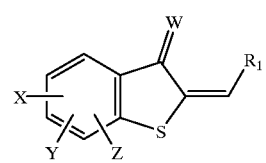

(I)

wherein W represents O, S, or $N(R_a)$, $R_a$ being hydrogen or an alkyl group of 1–5 carbon atoms; X, Y and Z may be the same or different and each represents hydrogen or a substituent selected from the group consisting of halogen, nitro, carboxy, hydroxy, alkyl of 1–5 carbon atoms, trifluoromethyl, alkoxy, acyloxy, cyano, amino, alkylamino, dialkylamino, sulfonamido, carboxamido, carbalkoxy, thio, alkylthio, alkylsufinyl and alkylsulfonyl;

$R_1$ represents a radical selected from those consisting of an unsubstituted or substituted heterocyclic group, an unsubstituted or substituted bicyclic ring moiety, an unsubstituted or substituted phenyl ($C_6H_5$) group, an unsubstituted or substituted biphenyl ($C_6H_5–C_5H_4$) group, an unsubstituted or substituted ω-phenylalkenyl ($C_6H_5(CH=CH)_n$) group, n being an integer from 1 to 5, such as phenylethenyl, an unsubstituted or substituted ω-phenylalkynyl ($C_6H_5(C≡C)_p$) group, p being an integer from 1 to 5, or an unsubstituted or substituted alkyl group of 1–5 carbon atoms which may be straight or branched chain, said heterocyclic group being selected from those consisting of furan, thiophene, oxazole, oxadiazole, pyridine, pyrimidine, pyrazole, triazole, pyridazine, 1,3-oxathiolane, thiazole, thiadiazole, imidazole, pyrrole, tetrazole and triazine, said bicyclic ring moiety being selected from those consisting of benzofuran, isobenzofuran, benzothiophene, isobenzothiophene, benzoxazole, benzopyrrole (indole), isoindole, benzpyrazole, quinoline, isoquinoline, 1,2-benzodiazine, 1,3-benzodiazine, 1,2,3-benzotriazole, benzothiazole, benzimidazole, 1,2,3-benzotriazine and 1,2,4-benzotriazine, the heterocyclic group and bicyclic ring moiety substituents being selected from those consisting of alkyl of 1–5 carbon atoms, halogen, alkoxy, hydroxy, nitro, or an unsubstituted or substituted phenyl group;

the phenyl group substituents, the biphenyl group substituents, the ω-phenylalkenyl group substituents and the ω-phenylalkynyl group substituents being at least one selected from those consisting of halogen, nitro, carboxy, hydroxy, alkyl of 1–5 carbon atoms, trifluoromethyl, alkoxy, acyloxy, cyano, amino, alkylamino, dialkylamino, sulfonamido, carboxamido, carbalkoxy, thio, alkylthio, alkylsulfinyl and alkylsulfonyl; the alkyl group substituents being at least one selected from those consisting of carboxy, hydroxy, alkoxy, amino, alkylamino, dialkylamino, thio or alkylthio, and the isomers and pharmaceutically acceptable salts of said compound.

In the compounds of formula I, above, the substituents of the heterocyclic group, the bicyclic ring moiety, the phenyl group, the biphenyl group, etc. may also be perhaloalkyl, dihaloalkyl, monohaloalkyl, and the heterocyclic group and the bicyclic ring moieties may also be substituted with carboxy, carbalkoxy, sulfo, sulfonate (i.e., sulfonic acid esters) thio, alkylthio, alkylsulfinyl or alkylsulfonyl substituents.

The above compounds may also be used for prevention of viral infections and disease associated with such infection in a susceptible host by administering to the host a prophylactically effective amount of the above-described compound or precursor thereof.

DETAILED DESCRIPTION OF THE INVENTION

The compounds used in the method of the invention can be conveniently prepared from known starting materials according to the general synthetic scheme illustrated below.

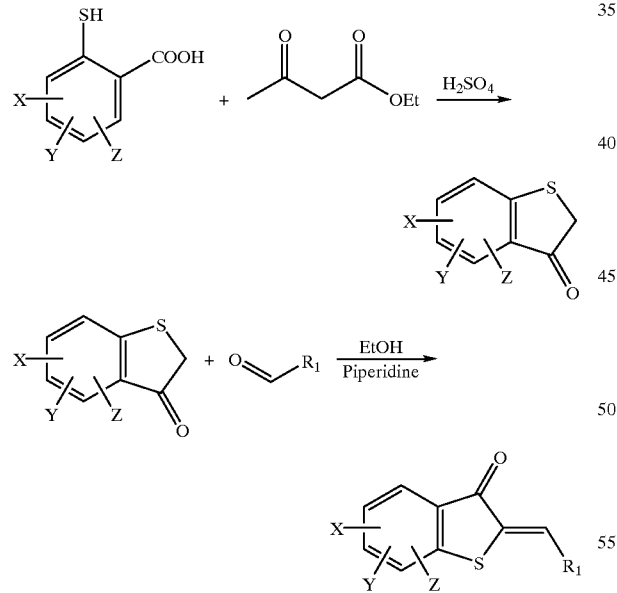

Preparations of specific anti-hepacivirus compounds which may be used in the practice of this invention are exemplified below.

In carrying out the above general synthetic scheme, the appropriate substituted 2-mercaptobenzoic acid, or an O-thioic or imidic acid analogue, in which X, Y and Z are as previously defined (prepared by known literature methods), is reacted with ethyl acetoacetate with a catalytic amount of concentrated sulfuric acid at 45–50° C. to give the substituted benzothiophenone. See, for example, Craik and Macbeth, J. Chem. Soc., 127: 1638 (1925); Smiles and McClelland, J. Chem. Soc., 119: 1813 (1921); and Hutchison and Smiles, J. Chem. Soc., 101: 573 (1912). Alternatively, the thionobenzothiophene analogue can be prepared by reaction of the appropriate benzothiophene with iodine in the presence of mercuric oxide, using benzene as the reaction medium, to yield 3-iodobenzothiophene, which is further reacted with magnesium and sulfur in the presence of iodine. See, for example, Ghaisas and Tilak, J. Sci. Ind. Res., 16B: 345–46 (1957). The iminobenzothiophene can be prepared from the same 3-iodobenzothiophene by treatment with aqueous ammonia. The two last-mentioned intermediates may exist in tautomeric forms. Reaction of these intermediates with any one of a variety of aldehydes, in which $R_1$ is as previously defined, in the presence of piperidine as a base, provides the desired product.

Other compounds useful in the practice of this invention may be similarly prepared, substituting the appropriate starting material(s) in the above reaction scheme.

In vitro studies have demonstrated the usefulness of compounds described herein as antiviral agents. Antiviral activity was measured by the inhibitory activity of the compounds against viral RdRp in an enzymological assay for RNA synthesis.

All possible isomers of formula I, above, are within the scope of the present invention. Representative examples of such isomers include, without limitation, cis and trans isomers.

The term "alkyl" as used herein refers to aliphatic hydrocarbon radicals of one to five carbon atoms in length. Similarly, the term "alkyl", or any variation thereof, used in combination form to name substituents such as alkoxy, alkylamino, or the like also refers to aliphatic hydrocarbon radicals of one to five carbon atoms in length.

The term "carboxamido", as used herein, refers to a radical or substituent of the formula —C(=O)—NR"R'", wherein R" and R'" represent hydrogen or alkyl.

The term "sulfonamido", as used herein, refers to a radical or substituent of the formula —SO$_2$NR" R'" or —NR"—SO$_2$R'", wherein R" and R'" are as previously defined.

Particularly useful in the practice of this invention are compounds, including isomeric forms, having the formula:

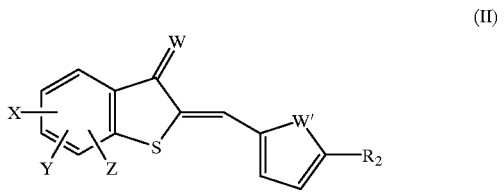

(II)

in which W, X, Y and Z are as previously defined, W' represents —O—, —S— or N($R_b$), $R_b$ being hydrogen or alkyl of 1–5 carbon atoms and $R_2$ represents H or unsubstituted or substituted phenyl, the phenyl substituents being at least one selected from those consisting of halogen, nitro, carboxy, hydroxy, alkyl of 1–5 carbon atoms, trifluoromethyl, trifluoromethoxy, acyloxy, alkoxy, cyano, amino, alkylamino, dialkylamino, sulfonamido, carbalkoxy, thio, alkylthio, alkylsulfinyl, alkylsulfonyl, or carboxamido and the isomers and pharmaceutically acceptable salts of said compounds. $R_2$ in formula II may also be a sulfo substituent.

The compounds of formulas I and II above and their pharmaceutically acceptable salts exhibit antiviral activity. The method of the invention is particularly effective against viruses of the Flaviviridae family and is useful in treating and/or preventing infections and diseases associated with these viruses in living hosts.

The compounds of the invention or precursors (e.g., prodrugs) thereof and their pharmaceutically acceptable salts are also useful in treating and preventing viral infections and diseases in living hosts when used in combination with supplemental active agents, including but not limited to interferons, ribavirin, protease inhibitors, immunoglobulins, immunomodulators, hepatoprotectants, anti-inflammatory agents, antibiotics, antivirals, anti-infectious agents, and the like.

Compounds described herein are also useful in preventing or resolving viral infections in cell, tissue or organ cultures and other in vitro applications. For example, inclusion of compounds of the invention as a supplement in cell or tissue culture growth media and cell or tissue culture components will prevent viral infections or contaminations of cultures not previously infected with viruses. Compounds described above may also be used to eliminate viruses from cultures or other biological materials infected or contaminated with viruses (e.g., blood), after a suitable treatment period, under any number of treatment conditions as determined by the skilled artisan.

Some of the compounds used in the method of the invention such as those containing basic substituents can form useful salts with various inorganic and organic acids, including, without limitation, hydrochloric or acetic acid, and those compounds containing acidic functionalities can form salts with inorganic and organic bases, including, without limitation, alkali metal hydroxides, alkaline earth metal hydroxides, piperidine, ammonium hydroxide, triethylamine or the like.

The pharmaceutically acceptable salts of the compounds of formulas I and II are prepared following procedures that are familiar to those skilled in the art.

The antiviral pharmaceutical compositions used in the method of the present invention comprise one or more of the compounds of formula I or II, above, as the active ingredient, and, optionally, at least one supplemental active agent, in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the antiviral compounds used in practicing the invention, such as by producing any undesirable biological effect or otherwise interacting in a deleterious manner with any other component(s) of the pharmaceutical composition, its use is contemplated to be within the scope of this invention.

In the pharmaceutical compositions of the invention, the active agent may be present in an amount of at least 0.5% and generally not more than 90% by weight, based on the total weight of the composition, including carrier medium and/or supplemental active agent(s), if any. Preferably, the proportion of active agent varies between 2–50% by weight of the composition.

Pharmaceutical organic or inorganic solid or liquid carrier media suitable for enteral or parenteral administration can be used to make up the composition. Gelatine, lactose, starch, magnesium stearate, talc, vegetable and animal fats and oils, gum, polyalkylene glycol, or other known carriers or excipients for medicaments may all be suitable as carrier media or excipients.

The compounds described above may be administered using any amount and any route of administration effective for attenuating infectivity of the virus. Thus, the expression "amount effective to attenuate virus infectivity", as used herein, refers to a nontoxic but sufficient amount of the antiviral agent to provide the desired treatment of viral infection. The exact amount required will vary from subject to subject, depending on the species, age, and general condition of the individual patient, the severity of the infection, the particular antiviral agent and its mode of administration, and the like.

The antiviral compounds are preferably formulated in dosage unit form for ease of administration and uniformity of dosage. "Dosage unit form" as used herein refers to a physically discrete unit of antiviral agent appropriate for the patient to be treated. Each dosage should contain the quantity of active material calculated to produce the desired therapeutic effect either as such, or in association with the selected pharmaceutical carrier medium. Typically, the antiviral compounds will be administered in dosage units containing from about 0.1 mg to about 500 mg of the antiviral agent by weight of the composition, with a range of about 1 mg to about 100 mg being preferred.

The antiviral compounds described herein may be administered as such, or in the form of a precursor from which the active agent can be derived, such as a prodrug. A prodrug is a derivative of a compound described herein, the pharmacologic action of which results from the conversion by chemical or metabolic processes in vivo to the active compound. Prodrugs include, without limitation, esters of the compounds of Formulas I or II, above, having carboxyl or hydroxyl functionalities. Such esters may be prepared from simple or functionalized aliphatic alcohols or carboxylic acids. Such prodrugs may be prepared according to procedures well known in the field of medicinal chemistry and pharmaceutical formulation science.

The antiviral compounds may be administered orally, rectally, parenterally, such as by intramuscular injection, subcutaneous injection, intravenous infusion or the like, intracisternally, intravaginally, intraperitoneally, locally, such as by powders, ointments, drops or the like, or by inhalation, such as by aerosol or the like, depending on the nature and severity of the infection being treated. Depending on the route of administration, the compounds of the invention may be administered at dosage levels of about 0.001 to about 120 mg/kg of subject body weight per day and preferably from about 0.01 to about 30 mg/kg of subject body weight per day, one or more times a day, to obtain the desired therapeutic effect.

By way of example, a suitable dose for oral administration would be on the order of 30 mg/kg of body weight per day, whereas a typical dose for intravenous administration would be on the order of 10 mg/kg of body weight per day.

These antiviral compounds will typically be administered from 1 to 4 times a day so as to deliver the above-mentioned daily dosage. However, the exact regimen for administration of the compounds and compositions described herein will necessarily be dependent on the needs of the individual host being treated, the type of treatment administered and the judgment of the attending medical specialist. As used herein, the term "host" includes both humans and animals.

In view of the inhibitory effect on viral RNA synthesis produced by the compounds used in the method of the invention, it is anticipated that these compounds will be useful not only for therapeutic treatment of virus infection, but for virus infection prophylaxis, as well. The dosages may be essentially the same, whether for treatment or prophylaxis of virus infection.

The following examples are provided to describe the invention in further detail. These examples, which set forth a preferred mode presently contemplated for carrying out the invention, are intended to illustrate and not to limit the invention.

The examples below illustrate the chemical synthesis of compounds used in the method of the invention.

EXAMPLE 1

Preparation of 4-(5-(3-Oxo-3H-benzo[b]thiophen-2-ylidenemethyl)furan-2-yl)benzoic Acid a.) Benzo-2,4-dihydrothiophene-3-one A mixture of 646 mg (4.19 mmoles) of thiosalicyclic acid, 680 mg (5.24 mmoles) of ethyl acetoacetate and a catalytic amount of sulfuric acid were heated to 45° C. to 50° C. for 4 hours. The mixture was poured over ice and a pink solid separated. The solid was collected and washed with water and hexane. The solid was then washed with ethylacetate and the mixture passed through a filter. The filtrate was concentrated to 557 mg of a pink colored solid.

b.) 5-Bromo-2-furancarboxaldehyde Dimethyl Acetal

A solution of 5.0 g (28.6 mmoles) of 5-bromo-2-furaldehyde, 4 ml of trimethylorthoformate and 10 mg pyridinium p-toluenesulfonate in 20 ml of dry methanol was heated to reflux under argon for 18 hours. The solution was concentrated to dryness and the crude yellow oil was passed through basic alumina, and eluted with 4:1 hexane:ethyl acetate to provide 6.03 g of product.

c.) 5-Tri-n-butylstanyl-2-furancarboxaldehyde Dimethyl Acetal

To a solution of 6.03 gm (0.0273 moles) of 5-bromo-2-furancarboxaldehyde dimethylacetal, prepared as in step b., above, in 75 ml of dry THF at −78° C. under argon was added 12 ml (1.1 eq) of 2.5M n-butyl lithium. After 10 minutes, the yellow solution was quenched with 8.88 g (1 eq) of tributyltin chloride, and the reaction slowly allowed to warm to room temperature. After extraction of the solution with water, drying the organic layer over anhydrous sodium sulfate and removal of the solvent, 11.3 g of product was obtained as a reddish oil.

d.) 5-(4-Carbethoxyphenyl)-2-furancarboxaldehyde Dimethyl Acetal

A suspension of 2.72 g (5.7 mmoles) of the product obtained in step c., above, 1.5 g (5.7 mmoles) of methyl 4-iodobenzoate and 204 mg (5 mol %) of palladium (II) chloride di-triphenylphosphine in 5 ml of dry tetrahydrofuran was heated to reflux under argon for 24 hours. Upon cooling, the dark brown solution solidified and the solid was washed with hexanes. The solid was dissolved in i-propyl acetate, filtered through basic alumina and the solution concentrated to an orange oil which was triturated with hexanes. A solid formed which was collected, washed with hexane and dried to give 1.0 g of product.

e.) 5-(4-Carboxyphenyl)-2-furancarboxaldehyde Dimethyl Acetal

A suspension of 865 mg (3.1 mmoles) of the ester derivative from step d., above, and 0.5 g of potassium hydroxide in 15 ml of methanol and 5 ml of water was heated to reflux under nitrogen for 48 hours. Upon cooling, the dark green mixture was concentrated to 5 ml, dissolved in ethyl acetate and water was added. The mixture was acidified with 1 ml of glacial acetic acid and the mixture was filtered through celite. The organic filtrate was washed several times with water and dried over sodium sulfate. After filtration, the solution was concentrated to dryness to provide 690 mg of an olive green solid.

f.) 5-(4-Carboxyphenyl)-2-furancarboxaldehyde

A solution of 690 mg of the acid derivative obtained from step e., above, and 10 mg of pyridinium p-toluenesulfonate in 100 ml of acetone was stirred at room temperature under argon for 48 hours. The suspension was concentrated to dryness and the residue suspended in a mixture of ethyl acetate and hexane, filtered and dried to provide 569 mg of a tan powder.

g.) 4-(5-(3-Oxo-3H-benzo[b]thiophen-2-ylidenemethyl)furan-2-yl)benzoic Acid

A mixture of 295 mg (1.96 mmoles) of the benzo-2,4-dihydrothiophene-3-one prepared as described in step a., above, 119 mg (0.55 mmoles) of the furancarboxaldehyde from step f.), above, 2 drops of piperidine and 10 ml of ethanol were heated under argon at 85° C. for 12 hours. The mixture was cooled to room temperature and 1 N hydrochloric acid was added to pH 1–2. 10 ml of t-butyl methylether was added and the solution was poured into 15 ml of water. An orange solid separated which was collected, washed with water and hexane and dried to give 175 mg of product.

EXAMPLE 2

Preparation of 4-(3-Oxo-3H-benzo[b]thiophen-2-ylidenemethyl)benzoic Acid

A suspension of 73 mg (0.48 mmol) of benzo-2,4-dihydrothiophen-3-one, 56 mg (0.37 mmol) of 4-carboxybenzaldehyde, and one drop of piperidine in 2 ml of absolute ethanol was heated at 80° C. under argon for 18 hours. Upon cooling to room temperature, the reaction mixture was adjusted to pH 2 with 1N HCl, and t-butyl methyl ether and water were added. The yellow-brown precipitate was collected by filtration, and air dried to yield 73 mg of the product as a yellow-brown solid.

EXAMPLE 3

Preparation of 2-(5-(2-Chloro-5-nitrophenyl)thiophen-2-ylmethylidene)benzo[b]thiophen-3-one a.) 5-Tri-n-butylstannylthiophene-2-carboxaldehyde Dimethyl Acetal This compound was prepared similarly to 5-Bromo-2-thiophenecarboxaldehyde dimethyl acetal as described in steps b. and c. of Example 1, above, starting from commercially available 5-bromo-thiophenecarboxaldehyde to yield 10.15 g of the product as an orange oil.

b.) 5-(2-Chloro-5-nitrophenyl)thiophene-2-carboxaldehyde Dimethyl Acetal

A suspension of 2.0 g (8.4 mmol) of 3-bromo-4-chloronitrobenzene, 4.16 g (9.2 mmol) of 5-tri-n-butylstannylthiophene-2-carboxaldehyde dimethyl acetal, prepared as in step a. of this example, and 0.297 g of palladium (II) chloride di-triphenylphosphine (5 mol %) in 20 ml of dry THF was refluxed under argon for 20 hours. Upon cooling to room temperature, the reaction was concentrated in vacuo to provide a red oil which was first passed through a plug of neutral alumina. The resultant red oil was subjected to preparatory HPLC (silica gel; 20% ethyl acetate/80% hexanes as eluents) and provided 1.93 g of the product as a viscous yellow oil.

c.) 5-(2-Chloro-5-nitrophenyl)thiophene-2-carboxaldehyde

A solution of 1.93 g of 5-(2-Chloro-5-nitrophenyl) thiophene-2-carboxaldehyde dimethyl acetal, prepared as in step b. of this example, and 10 mg of pyridinium p-toluenesulphonate in 100 ml of acetone was stirred at room temperature under argon for 20 hours. The yellow solution was concentrated in vacuo, and the crude product dissolved in ethyl acetate. The organic phase was washed with water (2×100 ml) before drying over anhydrous sodium sulfate. Concentration provided 1.46 g of the product as a yellow powder.

d.) 2-(5-(2-Chloro-5-nitrophenyl)thiophen-2-ylmethylidene)benzo[b]thiophen-3-one A suspension of 73 mg (0.48 mmol) of benzo-2,4-dihydrothiophen-3-one, 100 mg (0.37 mmol) of 5-(2-chloro-5-nitrophenyl)thiophene-2-carboxaldehyde, prepared as in step c. of this example, and 1 drop of piperidine in 2 ml of absolute ethanol was heated at 80° C. under argon for 18 hours. Upon cooling, water and t-butyl methylether was added, and the orange precipitate collected by filtration. The solid was washed with water followed by t-butyl methyl ether to provide 0.145 g of the product as an orange solid, mp 215–216° C.

Other compounds useful in the practice of this invention may be similarly prepared by substituting alternative 2-mercaptobenzoic acids and aldehyde reactants for those described in Example 1, above.

EXAMPLE 4

Inhibition of Viral RNA Replication

The discovery of inhibitors of viral polymerases and related proteins generally requires the evaluation of large numbers of chemical compounds or mixtures of chemical compounds. Thus, an assay for the polymerase activity that is capable of high volume screening, in other words, a high-throughput assay, is desirable. There are a variety of assay methodologies well known to the trained artisan that allow the efficient screening of large numbers of samples. See, for example, Cole, J L, Meth Enzymology, 275: 310–328 (1996). Any one of these assays may be suitable in the case of a viral RdRp activity.

One approach for measuring viral RdRp activity in the case of viruses of the Flaviviridae uses a purified recombinant NS5 protein in an in vitro RdRp assay. For example, Behrens et al., EMBO J., 15: 12–22 (1996) and Lohmann et al., J. Virol., 71: 8416–8428 (1997), describe the baculovirus expression, purification and enzymatic activity of the HCV NS5B RdRp. The bacterial expression, purification and enzymatic activity of the HCV NS5B RdRp protein has been disclosed in PCT/US96/15571 [WO 97/12033] and by Yuan et al. [Biochem Biophys Res Comm, 232:231–235 (1997)]. In a further example, Collett, PCT/US99/07404, which is commonly owned with the present application, discloses compositions comprising functional HCV NS5B sequences and their use in identifying compounds useful in the treatment of hepacivirus infections. As with the above examples for the HCV RdRp, bacterially-expressed dengue flavivirus NS5 protein has been purified and shown to exhibit RdRp activity [Tan et al., Virology, 216: 317–325 (1996)], as has the NS5B protein of the pestivirus BVDV purified from recombinant baculovirus-infected cells [Zhong et al., J. Virol., 72: 9365–9369 (1998)].

By way of example, the inhibitory activity of candidate antiviral compounds may be determined by using NS5 proteins prepared essentially according to Collett, PCT/US99/07404, in in vitro RdRp assays. Purified NS5 proteins are incubated in standard RdRp reaction mixtures. Such reaction mixtures generally consist of buffers, salts, cations, reducing agents and the like, as well as nucleoside triphosphates and an RNA template-primer. Variations in the individual components of such reaction mixtures may be required to accommodate the particular reaction preferences of individual NS5 proteins. Such variations are well known to the trained artisan. Representative compounds falling within formula I, above, as shown in Examples 1–3 and Table 1, below, were evaluated for antiviral activity using this assay. Inhibitory activity of the compounds tested was expressed in $IC_{50}$ values. $IC_{50}$ values represent the concentration of the compound at which 50% of the RdRp activity is inhibited. The results of the assay for inhibition of RdRp activity in at least one virus of the Flaviviridae family for the compounds tested revealed $IC_{50}$ values ranging from 0.2 $\mu$M to about 30 $\mu$M.

The low concentrations of test compounds capable of achieving 50% inhibition of HCV RdRp activity indicate that the method of the invention is effective at inhibiting RNA synthesis by the viral RdRp enzymes involved in Flaviviridae replication.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

TABLE 1

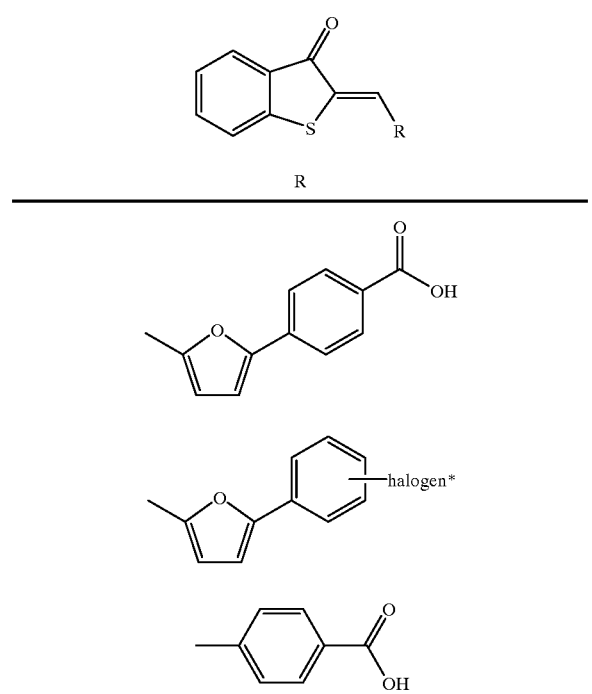

TABLE 1-continued

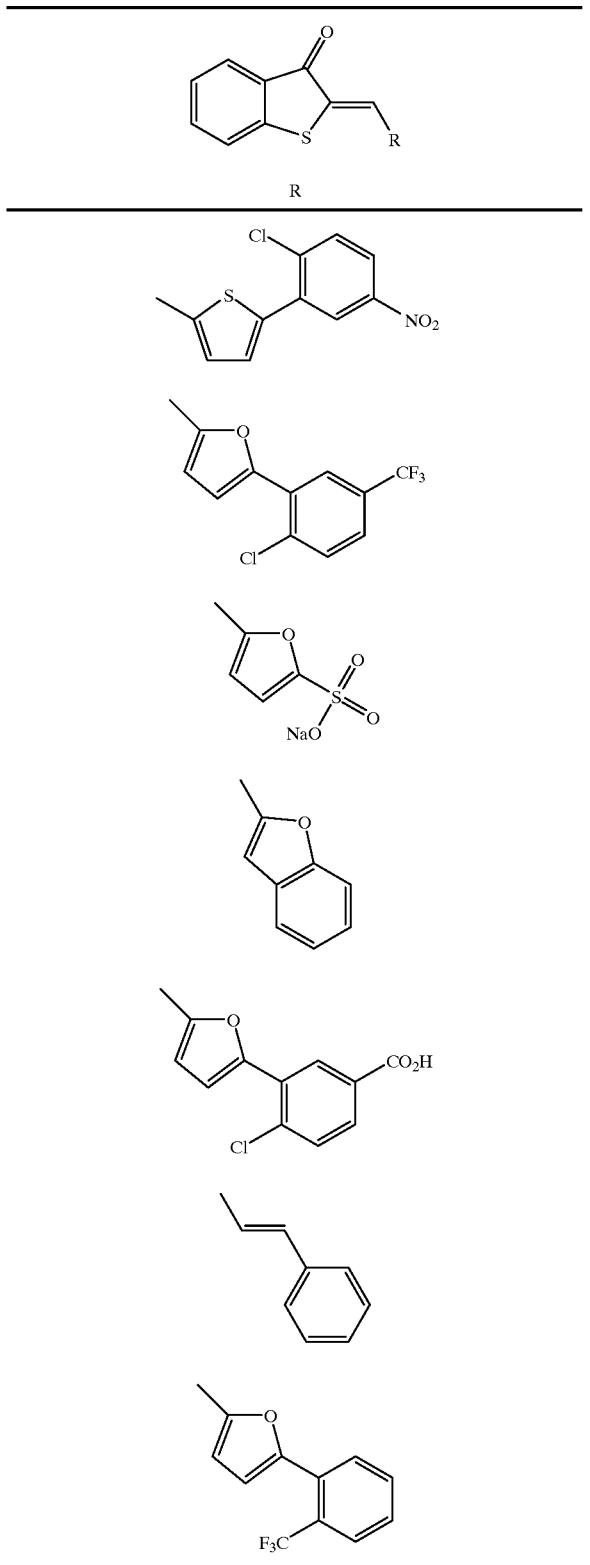

*o-chloro, m-chloro, p-chloro and p-bromo

What is claimed is:

1. A method of treating infection caused by at least one virus of the Flaviviridae family and disease associated with said infection in a living host having said infection, said method comprising administering to said host a therapeutically effective amount of a compound, or a precursor of said compound, having the formula:

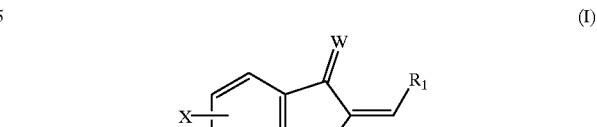

(I)

wherein W represents O, S, or $N(R_a)$, $R_a$ being hydrogen or an alkyl group of 1–5 carbon atoms; X, Y and Z may be the same or different and each represents hydrogen or a substituent selected from the group consisting of halogen, nitro, carboxy, hydroxy, alkyl of 1–5 carbon atoms, trifluoromethyl, alkoxy, acyloxy, cyano, amino, alkylamino, dialkylamino, sulfonamido, carboxamido, carbalkoxy, thio, alkylthio, alkylsufinyl and alkylsulfonyl;

$R_1$ represents a radical selected from those consisting of an unsubstituted or substituted heterocyclic group, an unsubstituted or substituted bicyclic ring moiety, an unsubstituted or substituted phenyl ($C_6H_5$) group, an unsubstituted or substituted biphenyl ($C_6H_5$–$C_5H_4$) group, an unsubstituted or substituted ω-phenylalkenyl ($C_6H_5(CH=CH)_n$) group, n being an integer from 1 to 5, an unsubstituted or substituted ω-phenylalkynyl ($C_6H_5(C\equiv C)_p$) group, p being an integer from 1 to 5, or an unsubstituted or substituted alkyl group of 1–5 carbon atoms which may be straight or branched chain, said heterocyclic group being selected from those consisting of furan, thiophene, oxazole, oxadiazole, pyridine, pyrimidine, pyrazole, triazole, pyridazine, 1,3-oxathiolane, thiazole, thiadiazole, imidazole, pyrrole, tetrazole and triazine, said bicyclic ring moiety being selected from those consisting of benzofuran, isobenzofuran, benzothiophene, isobenzothiophene, benzoxazole, benzopyrrole, isoindole, benzpyrazole, quinoline, isoquinoline, 1,2-benzodiazine, 1,3-benzodiazine, 1,2,3-benzotriazole, benzothiazole, benzimidazole, 1,2,3-benzotriazine and 1,2,4-benzotriazine, the heterocyclic group and bicyclic ring moiety substituents being selected from those consisting of alkyl of 1–5 carbon atoms, halogen, alkoxy, hydroxy, nitro, perhaloalkyl, dihaloalkyl, monohaloalkyl, carboxy, carbalkoxy, sulfo, sulfonate, thio, alkylthio, alkylsulfinyl, alkylsulfonyl or an unsubstituted or substituted phenyl group;

the phenyl group substituents, the biphenyl group substituents, the ω-phenylalkenyl group substituents and the ω-phenylalkynyl group substituents being at least one selected from those consisting of halogen, nitro, carboxy, hydroxy, alkyl of 1–5 carbon atoms, perhaloalkyl, dihaloalkyl, monohaloalkyl, alkoxy, acyloxy, cyano, amino, alkylamino, dialkylamino, sulfonamido, carboxamido, carbalkoxy, thio, alkylthio, alkylsulfinyl and alkylsulfonyl; the alkyl group substituents being at least one selected from those consisting of carboxy, hydroxy, alkoxy, amino, alkylamino, dialkylamino, thio or alkylthio, and the isomers and pharmaceutically acceptable salts of said compound.

2. A method as claimed in claim 1, wherein said compound is administered in unit dosage form containing about 0.001 to about 120 mg of said compound per kilogram of patient body weight per day.

3. A method as claimed in claim 2, wherein said unit dosage includes a pharmaceutically acceptable carrier medium.

4. A method as claimed in claim 1, wherein a precursor of said compound is administered in the form of a prodrug.

5. A method as claimed in claim 1, wherein said compound or a precursor of said compound is administered in combination with at least one supplemental active agent selected from the group consisting of interferons, ribavirin, protease inhibitors, immunoglobulins, immunomodulators, hepatoprotectants, anti-inflammatory agents, antibiotics, antivirals or anti-infectious agents.

6. A method as claimed in claim 5, wherein said compound or precursor of said compound and said at least one supplemental active agent are administered simultaneously.

7. A method as claimed in claim 1, wherein said route of administration is selected from the group consisting of orally, rectally, parenterally, intracisternally, intravaginally, intraperitoneally, locally or by inhalation.

8. A method of prophylactically treating infection caused by at least one virus of the Flaviviridae family and disease associated with said infection in a living host susceptible to said infection, said method comprising administering to said host a prophylactically effective amount of a compound, or a precursor of said compound, having the formula:

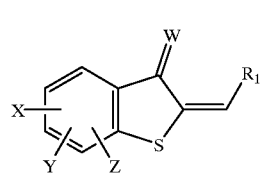

(I)

wherein W represents O, S, N($R_a$), $R_a$ being hydrogen or an alkyl group of 1–5 carbon atoms; X, Y and Z may be the same or different and each represents hydrogen or a substituent selected from the group consisting of halogen, nitro, carboxy, hydroxy, alkyl of 1–5 carbon atoms, trifluoromethyl, alkoxy, acyloxy, cyano, amino, alkylamino, dialkylamino, sulfonamido, carboxamido, carbalkoxy, thio, alkylthio, alkylsufinyl and alkylsulfonyl;

$R_1$ represents a radical selected from those consisting of an unsubstituted or substituted heterocyclic group, an unsubstituted or substituted bicyclic ring moiety, an unsubstituted or substituted phenyl ($C_6H_5$) group, an unsubstituted or substituted biphenyl ($C_6H_5$–$C_5H_4$) group, an unsubstituted or substituted ω-phenylalkenyl ($C_6H_5(CH=C)_n$) group, n being an integer from 1 to 5, an unsubstituted or substituted ω-phenylalkynyl ($C_6H_5(C\equiv C)_p$) group, p being an integer from 1 to 5, or an unsubstituted or substituted alkyl group of 1–5 carbon atoms which may be straight or branched chain, said heterocyclic group being selected from those consisting of furan, thiophene, oxazole, oxadiazole, pyridine, pyrimidine, pyrazole, triazole, pyridazine, 1,3-oxathiolane, thiazole, thiadiazole, imidazole, pyrrole, tetrazole and triazine, said bicyclic ring moiety being selected from those consisting of benzofuran, isobenzofuran, benzothiophene, isobenzothiophene, benzoxazole, benzopyrrole, isoindole, benzpyrazole, quinoline, isoquinoline, 1,2-benzodiazine, 1,3-benzodiazine, 1,2,3-benzotriazole, benzothiazole, benzomidazole, 1,2,3-benzotriazine and 1,2,4-benzitriazine, the heterocyclic group and bicyclic ring moiety substituents being selected from those consisting of alkyl of 1–5 carbon atoms, halogen, alkoxy, hydroxy, nitro, perhaloalkyl, dihaloalkyl, monohaloalkyl, carboxy, carbalkoxy, sulfo, sulfonate, thio, alkylthio, alkylsulfinyl, alkylsulfonyl or an unsubstituted or substituted phenyl group;

the phenyl group substituents, the biphenyl group substituents, the ω-phenylalkenyl group substituents and the ω-phenylalkynyl group substituents being at least one selected from those consisting of halogen, nitro, carboxy, hydroxy, alkyl of 1–5 carbon atoms, perhaloalkyl, dihaloalkyl, monohaloalkyl, alkoxy, acyloxy, cyano, amino, alkylamino, dialkylamino, sulfonamido, carboxamido, carbalkoxy, thio, alkylthio, alkylsulfinyl and alkylsulfonyl; the alkyl group substituents being at least one selected from those consisting of carboxy, hydroxy, alkoxy, amino, alkylamino, dialkylamino, thio or alkylthio, and the isomers and pharmaceutically acceptable salts of said compound.

9. A method as claimed in claim 8, wherein said compound is administered in unit dosage form containing about 0.001 to about 120 mg of said compound per kilogram of patient body weight per day.

10. A method as claimed in claim 9, wherein said unit dosage includes a pharmaceutically acceptable carrier medium.

11. A method as claimed in claim 8, wherein a precursor of said compound is administered in the form of a prodrug.

12. A method as claimed in claim 8, wherein said compound or a precursor of said compound is administered in combination with at least one supplemental active agent selected from the group consisting of interferons, ribavirin, protease inhibitors, immunoglobulins, immunomodulators, hepatoprotectants, anti-inflammatory agents, antibiotics, antivirals or anti-infectious agents.

13. A method as claimed in claim 12, wherein said compound or precursor of said compound and said at least one supplemental active agent are administered simultaneously.

14. A method as claimed in claim 8, wherein said route of administration is selected from the group consisting of orally, rectally, parenterally, intracisternally, intravaginally, intraperitoneally, locally or by inhalation.

* * * * *